(12) United States Patent
Kaul et al.

(10) Patent No.: US 6,339,084 B1
(45) Date of Patent: Jan. 15, 2002

(54) PROCESS FOR THE PRODUCTION OF THIAZINE-INDIGO PIGMENTS

(75) Inventors: Bansi Lal Kaul, Biel-Benken (CH); Bruno Piastra, Huningue (FR)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/620,271

(22) Filed: Jul. 19, 2000

Related U.S. Application Data

(63) Continuation of application No. 09/275,533, filed on Mar. 24, 1999.

(30) Foreign Application Priority Data

Mar. 25, 1998 (GB) ............................................. 9806220

(51) Int. Cl.[7] ............................................. A61K 31/54
(52) U.S. Cl. ............................. 514/224.2; 514/227.5; 544/52
(58) Field of Search ........................... 514/224.2, 227.5; 544/52

(56) References Cited

U.S. PATENT DOCUMENTS 3,803,139 A    4/1974   Kaul .......................... 260/243

FOREIGN PATENT DOCUMENTS

GB    1 358 574    7/1974

OTHER PUBLICATIONS

Article, "Studies on Heterocyclic Colouring Matters" by B.L. Kaul, Helvetica Chemica Acta, vol. 57 (8), 1974, pp. 2264–2678.

Primary Examiner—Mukund J. Shah
Assistant Examiner—Tamthom N. Truong
(74) Attorney, Agent, or Firm—Susan S. Jackson; Scott E. Hanf

(57) ABSTRACT

A process of forming the cis- or the trans-isomers of thiazine-indigo compounds comprising the step of reacting o-aminomercapto-carbocyclic or -heterocyclic compounds with a maleic acid or fumaric acid derivative in the presence of an aqueous system.

The invention further relates to a process of converting cis-isomers of thiazine-indigo compounds into the trans-isomers being pigments.

The invention also relates to the cis-isomers of thiazine-indigo compounds of formula I as defined in claim 14 which are new compounds.

17 Claims, No Drawings

PROCESS FOR THE PRODUCTION OF THIAZINE-INDIGO PIGMENTS

CROSS-REFERENCE TO RELATED APPLICATIONS

This application is a continuation of U.S. application Ser. No. 09/275,533, filed on Mar. 24, 1999.

FIELD OF THE INVENTION

This invention relates to a new process of forming cis- or trans-thiazine-indigo compounds in aqueous media. This invention also relates to a process of converting the cis-thiazine-indigo compounds into the trans-thiazine-indigo isomers, which are known to be pigments.

BACKGROUND OF THE INVENTION

Thiazine-indigo compounds are an important series of pigments. Prior art processes for forming these pigments involve the reaction of certain o-aminomercapto-carbocyclic or -heterocyclic compounds with maleic acid or a derivative thereof in the presence of a solvent. Solvents useful for this purpose were either a carboxylic acid (which also acted to catalyze the reaction) or an inert polar aprotic solvent.

Thus, in DE 2151723 a process is described for making certain symmetrically substituted benzothiazine-indigo compounds wherein certain substituted ortho-aminomercapto-carbocyclic or heterocyclic compounds are reacted with a maleic acid derivative in a carboxylic acid, e. g. acetic acid. By symmetrically substituted is meant that there is identical substitution on each of the thiazine rings.

In DE-OS 2536120 a process is described for making certain other symmetrically substituted benzothiazine-indigo compounds wherein certain substituted ortho-aminothiophenols are reacted with a maleic acid derivative in an inert polar aprotic solvent. It is alleged that the benzothiazine-indigo compounds so formed, display improved pigmentary properties, e. g. brighter and cleaner shade over the compounds made in a carboxylic acid solution, however, they can only be produced in poor yield.

There still remains a need to provide a further improved process of forming thiazine-indigo compounds, especially tans-thiazine-indigo pigments.

SUMMARY OF THE INVENTION

Accordingly, the invention provides in one of its aspects an environmentally friendly water-based process of forming thiazine-indigo compounds according to the formula (I) [cis-isomers] and (II) [trans-isomers]

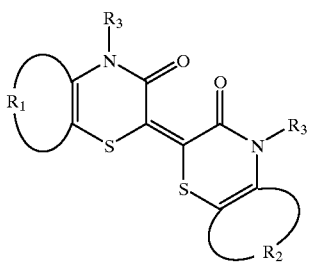

(I)

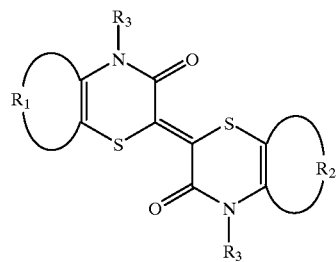

(II)

wherein
$R_1$ and $R_2$ independently represent the atoms necessary to complete the formation of a substituted or unsubstituted aromatic or aliphatic carbocyclic or heterocyclic ring system, and
$R_3$ is hydrogen, $C_{1-12}$alkyl or phenyl,
comprising the step of reacting in the presence of an aqueous system compounds of formula (IIIa) and (IIIb)

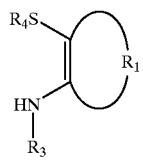

(IIIa)

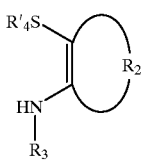

(IIIb)

wherein
$R_4$ and $R'_4$ independently are H or a metallic ion selected from $Na^+$, $K^+$ or $Zn^{2+}$
with a compound of formula m [trans-isomers] or (V) [cis-isomers]

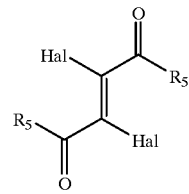

(IV)

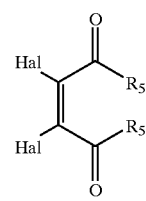

(V)

wherein
Hal is Cl or Br,
both $R_5$ independently are a leaving group commonly used in substitution reactions at carbonyl carbon atoms, e. g. Cl or $C_{1-5}$-alkoxy or OH.

DESCRIPTION OF THE PREFERRED EMBODIMENTS

The aqueous system comprises water or water and an acidic catalyst or water and a basic catalyst or a mixture of water and a water miscible solvent, like alcohols.

Particularly interesting is the possibility to use dihalomaleic acids or dihalomaleic acids, already prepared or generated in situ.

It has been discovered that fumaric derivatives of formula (IV) give the trans-isomer of formula (II) and the maleic derivatives of formula (V) give the cis-isomer of formula (I).

Preferably the molar ratio of the reactants is 1:1:1.

The process is carried out in the presence of a carboxylic acid or of a salt thereof, e. g. acetic acid, or an inorganic acid or salt thereof, e. g. sulphuric acid or hydrochloric acid or phosphoric acid, which also acts as a catalyst, and an aqueous medium, e. g. water or a mixture of water and a miscible solvent, preferably an alcohol with 1–5 C-atoms, e. g. ethanol, methanol or butanol.

The basic catalyst is an inorganic base, especially sodium or potassium hydroxide or an organic base such as triethylamine.

The reaction is preferably carried out in water in the presence of 0 to 95% by weight, preferably 10% by weight of an acid catalyst, e. g. acetic acid or hydrochloric acid or sulphuric acid or phosphoric acid.

The reaction temperature is preferably of the order of 0 to 150° C., more preferably between 10 and 100°C.

Compounds of formulae (IIIa), (IIIb), (IV) and (V) are known compounds or can be prepared in analogy to known methods.

The thiazine-indigo compounds of formulae (I) and (II) may be symmetrically substituted, that is $R_1$ and $R_2$ are identical. Alternatively, they may be asymmetrically substituted, that is, $R_1$ and $R_2$ are not identical. Non-identity refers to either the ring systems $R_1$ and $R_2$ being different or, in the event that the ring systems are identical, the substituents attached to the respective ring systems are different.

Preferred thiazine-indigo compounds formed according to the invention are those asymmetric compounds wherein $R_1$ and $R_2$ are independently selected from the group consisting of

(a)

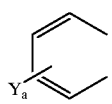

(b)

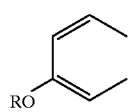

(c)

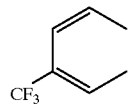

(d)

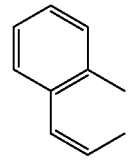

(e)

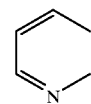

(f)

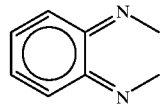

(g)

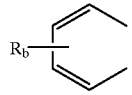

(h)

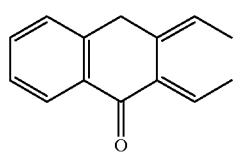

(i)

wherein
Y is halogen which includes F, Cl and Br, especially Cl
R is $C_{1-4}$alkyl, especially methyl or ethyl
a is 1, 2, 3 or 4
b is 1, 2, 3 or 4.

In a more preferred process according to the invention, $R_1$ consists of the atoms necessary to complete a benzene ring which is optionally substituted with, for example halogen or alkyl and $R_2$ consists of the atoms necessary to complete a ring system which is a symmetrically substituted benzene ring or a different ring system, e. g. naphthalene, pyridine or 1,4-benzodiazine.

The thiazine-indigo pigments formed according to the invention may be substituted on the ring systems with one or more of any of the non-water-solubilising substituents common in the art of pigments. Preferably the ring system substituents are selected from the group consisting of halogen, trifluoromethyl, nitro, cyano, alkyl, alkoxy, amino, alkylamino, thioalkyl, phenoxy, phenylamino, phenylthio, acyl, acyloxy or acylamino.

The term "halogen" includes fluorine and especially chlorine and bromine. The term "alkyl" or "alkoxy" comprises preferably radicals with 1 to 4 carbon atoms. The terms "alkylamino" and "phenylamino" include for example N,N-dialkylamino and N,N-diphenylamino as well as N-monoalkyamino and N-monophenylamino.

The aforementioned alkyl, alkoxy, phenyl and phenoxy substituents may themselves contain one or more substituents selected from the substituents hereinabove described.

A further aspect of the invention relates to the cis-isomers of formula I which are new compounds except of the compound of example 1 in which $R_1$ and $R_2$ are benzene rings.

Another aspect of the invention is the process of converting the cis-isomer of formula (I) into the trans-isomer of formula (II), by thermal treatment in an inert polar solvent, in the presence or not of an acidic catalyst, that can be a carboxylic acid, e. g. acetic acid, trifluoromethane sulfonic acid or para-toluene sulfonic acid or another acid usually used in organic chemistry.

The inert polar solvent can be chlorobenzene, nitrobenzene, dimethylformamide, dimethylacetamide, N-methylpyrrolidone, or a high boiling point alcohol, like ethylene glycol, dipropylene glycol methyl ether.

The thermal treatment comprises temperatures of from 100 to 250° C., preferably of from 100 to 180° C., more preferably of from 130 to 160° C.

The trans-thiazine-indigo pigments formed by the conversion process according to the invention are suitable for the mass pigmentation of suitable substrates including synthetic polymers, synthetic resins and regenerated fibers optionally in the presence of solvents. These substrates more particularly include oil, water and solvent based surface coatings, polyester spinning melts, polyethylene, polystyrene and polyvinyl chloride molding materials, rubber and synthetic leather. Furthermore, the pigments can be used in the manufacture of printing inks, for the mass coloration of paper and for coating and printing textiles.

Based on the substrate to be mass pigmented the thioazine-indigo pigments according to the invention are used in amounts of 0.01 to 30% by weight, preferably 0.1 to 10% by weight When applied to the afore-mentioned substrates the thiazine-indigo pigments are found to be resistant to migration and fast to light, and show fastness to washing, chlorite, hypochlorite and peroxide bleaching, rubbing, overspraying and solvents. Notably, the pigments display high tinctorial power, good transparency and good heat stability.

The invention is further illustrated by means of the following examples in which all percentages and all quantities are expressed by weight.

EXAMPLE 1
Preparation of a cis-thiazine-indigo Compound 27 g of o-aminothiophenol are dropped at 20° C. during 30 min into a solution of 20 g of 2,3-dichloromaleic acid in 200 ml of water containing 2 ml of the dispersing agent Sandopan 2 N, under a nitrogen atmosphere. A yellow precipitate rapidly appears. The mixture is then heated under reflux for 5 hours. The suspension is then filtered hot and washed out with 1000 ml of warmed water. The product is then dried at 80° C. under vacuum overnight. 32.4 g of a yellow product is obtained. This product is the cis-thiazine-indigo compound of the following formula and is soluble in polar organic solvent.

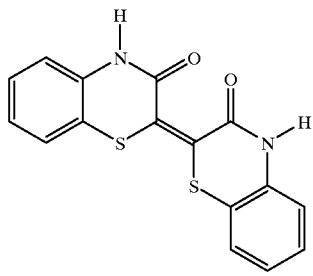

MS (APCI, positive ionization): 349 [M+Na]$^+$; 327 [M+H]$^+$)
MS (APCI, negative ionization): 325 [M–H]$^+$; 299; 281; 150

EXAMPLE 2
Isomerization of a cis-thiazine-indigo Compound into the trans-thiazine-indigo Pigment The 32.4 g of the yellow compound prepared in the example 1 is dispersed in 150 ml of dimethylformamide and then heated to 120° C. for 4 hours. The isomerisation occurs during this thermal treatment, the initial yellowish orange suspension becomes red and thicker. The pigment is then filtered at 100° C. washed with 400 ml of dimethylformamide and 100 ml of ethanol. The product is dried at 80° C. under vacuum overnight. 20.4 g of a bright red orange solid being the trans-thiazine-indigo isomer of the following formula

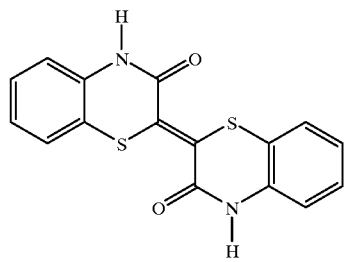

is obtained.

EXAMPLE 3
Preparation of a cis-thiazine-indigo Compound 50 g of o-aminothiophenol are dropped during 15 min a solution of 300 mnl of water and 52 g of sodium hydroxide 30.8%, under a nitrogen atmosphere. The mixture is stirred for 20 min. Then it is filtered for eliminating a yellow precipitate, which is the disulfide. To a solution of 37 g of 2,3-dichloromaleic acid and 100 ml of water which has been cooled to 10° C. is then added the solution of the sodium o-aminothiophenolate during one hour whilst keeping the temperature at 10° C. The mixture is then gradually heated to reflux, and further heated for 4 hours. The yellow suspension is filtered hot and washed out with 1.5 liters of hot water. The product is dried at 80° C. under vacuum overnight 57 g of a yellow solid being the cis-thiazine-indigo isomer of the following formula

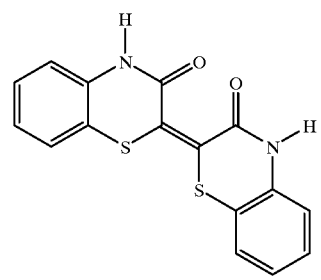

is obtained.

EXAMPLE 4
Preparation of a trans-thiazine-indigo Pigment Followed by a Purification Process A 750 ml reactor is charged with 150 ml of water and 60.8 g of acetylenedicarboxylic acid monopotassium salt. 19.6 g of potassium hydroxide are added and the pH adjusted to pH 7 with 3.35 ml of sodium hydroxide 30.8%. 51.5 g of sodium bromide are added to the mixture and 64 g of bromine are dropped during one hour, keeping the temperature below 25° C. The stirring is continued for 2 hours. A solution of sodium o-aminothiophenolate which is prepared according to the procedure described in the example 3 from 100 g of o-aminothiophenol and 100 g of sodium hydroxide 30.8% and 300 ml of water, is added at 50° C. during 2 hours. 30 ml of concentrated sulphuric acid are then added. The mixture is then refluxed for 2 hours, then filtered and washed with hot water. The crude product which contains trans-thiazine-indigo and impurities is reslurried in 350 ml of dimethylacetamide and heated at 90° C. for 8 hours. There is no isomerisation at this temperature, it is just a purification process. The suspension is filtered at 80° C. and washed with 1 liter of dimethylacetamide and 500 ml of ethanol. The product is dried at 80° C. under vacuum overnight. 35 g of a red solid being the trans-thiazine-indigo isomer of the following formula

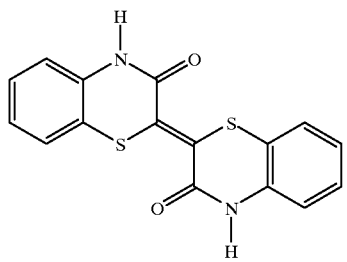

is obtained.

EXAMPLE 5
Preparation of a cis-thiazine-indigo Compound 50 g of o-aminothiophenol are dropped during 15 min in a solution of 200 ml of water and 52 g of sodium hydroxide 30.8%, under a nitrogen atmosphere. The mixture is stirred for 20 min. Then it is filtered for eliminating a yellow precipitate, which is the disulfide. To a solution of 37 g of 2,3-dichloromaleic acid and 150 ml of phosphate buffer pH 2 at 20° C. is then added the solution of the sodium o-aminothiophenolate during 90 min whilst keeping the temperature below 25° C. The mixture is then gradually heated to reflux, and further heated for 4 hours. The yellow suspension is filtered hot and washed out with 1.5 liters of hot water. The product is dried at 80° C. under vacuum overnight. 60 g of a yellow solid that is the cis-thiazine-indigo isomere is obtained.

EXAMPLE 6
Preparation of a cis-7,7'-dichlorobenzothiazine-indigo Compound and isomerisation into the trans-7,7'-dichlorobenzothiazine-indigo A reactor is charged with 144.5 g of 30% concentrated sodium hydroxide, 55.5 g of sodium hydroxide, 92.25 g of 2-amino-6-chlorobenzothiazole. The mixture is then heated at reflux for 24 hours. After that, the mixture is allowed to cool at 20° C., diluted with 200 ml of water. 137 g of concentrated hydrochloric acid are dropped into the reactor. Another reactor is charged with 46.25 g of dichloromaleic acid, 300 ml of water, 30 g of acetic acid and 3 ml of the dispersing agent Sandopan 2N. The sodium 2-amino-5-chlorothiophenolate of the first reactor is then added to the content of the second reactor during one hour. An orange solid is formed, and then the reaction mixture is heated to reflux for 3 hours. The orange suspension is filtered hot and washed out with 1.5 liters of hot water. 120 g of a wet crude product being cis-7,7'-dichlorothiazine-indigo compound in majority is obtained. This crude product is reslurried in 120 ml of dimethylacetamide and heated at 150° C. for 5 hours. The mixture becomes red, indicating that the cis to tans conversion takes place. The red solid is then filtered hot, washed with 500 ml of hot dimethylacetamide and 150 ml of ethanol. The product is dried at 80° C. under vacuum overnight. 27.1 g of 7,7'-dichlorobenzothliazine-indigo pigment of the following formula

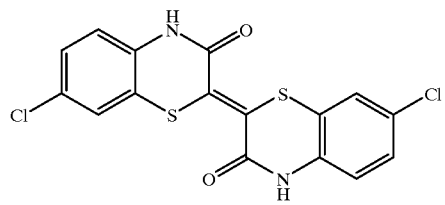

are obtained.

What is claimed is:
1. A process of forming thiazine-indigo compounds of formula (I) (cis-isomers) and of formula (II) (trans-isomers)

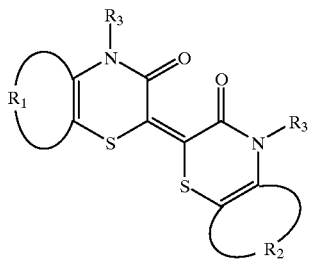

(I)

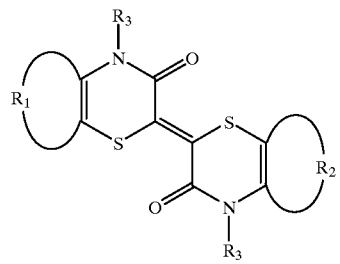

(II)

wherein
R$_1$ and R$_2$ independently represent the atoms necessary to complete the formation of a substituted or unsubstituted aromatic or aliphatic carbocyclic or heterocyclic ring system, and
R$_3$ is hydrogen, C$_{1-12}$alkyl or phenyl,
comprising reacting in the presence of an aqueous system comprising water or water and a further component selected from the group consisting of acidic catalysts and basic catalysts; compounds of formulae (IIIa) and (IIIb)

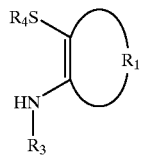

(IIIa)

-continued

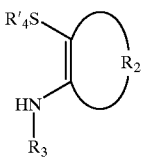
(IIIb)

wherein
R$_4$ and R'$_4$ independently are H or a metallic ion selected from Na$^+$, K$^+$, or Zn$^{2+}$ with a compound of formula (IV) (bans isomers) or (V) (cis-isomers)

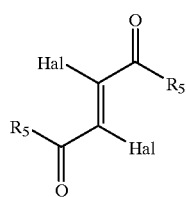
(IV)

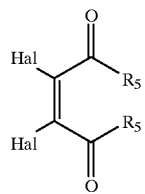
(V)

wherein
Hal is Cl or Br,
both R$_5$ independently are a leaving group commonly used in substitution reactions at carbonyl carbon atoms.

2. The process according to claim 1 wherein R$_5$ is selected from the group consisting of Cl, C$_{1-5}$alkoxy, and OH.

3. The process according to claim 1 wherein the acidic catalyst is a carboxylic acid or an inorganic acid or salts thereof.

4. The process according to claim 2 wherein the carboxylic acid is acetic acid.

5. The process according to claim 2 wherein the inorganic acid is sulphuric or hydrochloric acid or phosphoric acid.

6. The process according to claim 1, wherein the basic catalyst is selected from the group consisting of sodium hydroxide, potassium hydroxide and triethylamine.

7. The process according to claim 1, wherein the aqueous system consists of 0 to 95% by weight of an acidic catalyst and 95 to 5% by weight of water.

8. The process according to claim 7, wherein the aqueous system consists of 10% by weight of an acidic catalyst and 90% by weight of water.

9. The process according to claim 1, wherein the molar ratio of the compounds (IIIa) to (IIIb) to (IV) or (V) is 1:1:1.

10. The process of converting a cis-thiazine indigo compound of formula (I) according to claim 1 into the trans-thiazine-indigo pigment of formula (II) according to claim 1 by thermal treatment in an inert polar solvent, optionally in the presence of an acidic catalyst wherein the solvent is selected from the group consisting of dimethylformamide, dimethylacetamide and N-methylpyrrolidone (NMP).

11. The process according to claim 10, wherein the thermal treatment comprises temperatures of from 100 to 250° C.

12. The process according to claim 11, wherein the thermal treatment comprises temperatures of from 100 to 180° C.

13. The process according to claim 12, wherein the thermal treatment comprises temperatures of from 130 to 160° C.

14. The process according to claim 10, wherein the acidic catalyst is a carboxylic acid.

15. The process according to claim 14, wherein the carboxylic acid is acetic acid.

16. The process according to claim 10, wherein the acidic catalyst is selected from the group consisting of trifluoromethane sulfonic acid and para-toluene sulfonic acid.

17. The process according to claim 10, wherein the inert polar solvent is selected from the group consisting of chlorobenzene, nitrobenzene, dimethylformamide, dimethylacetamide, N-methylpyrrolidone, ethylene glycol and dipropylene glycol methyl ether.

* * * * *